(12) United States Patent
Dalton et al.

(10) Patent No.: US 6,492,554 B2
(45) Date of Patent: Dec. 10, 2002

(54) SELECTIVE ANDROGEN RECEPTOR MODULATORS AND METHODS OF USE THEREOF

(75) Inventors: James T. Dalton, Columbus, OH (US); Duane D. Miller, Germantown, TN (US); Donghua Yin, Columbus, OH (US); Yali He, Florence, SC (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/935,044

(22) Filed: Aug. 23, 2001

(65) Prior Publication Data

US 2002/0099036 A1 Jul. 25, 2002

Related U.S. Application Data

(63) Continuation of application No. 09/644,970, filed on Aug. 24, 2000, now abandoned.
(60) Provisional application No. 60/300,083, filed on Jun. 25, 2001.

(51) Int. Cl.$^7$ .............................................. C07C 233/05
(52) U.S. Cl. ..................... 564/158; 564/153; 564/157
(58) Field of Search ................................... 514/522, 524, 514/616, 628; 564/157, 158, 153; 558/414

(56) References Cited

U.S. PATENT DOCUMENTS

| | | | |
|---|---|---|---|
| 3,875,229 A | 4/1975 | Gold | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,465,507 A | 8/1984 | Konno et al. | |
| 4,636,505 A | 1/1987 | Tucker | |
| 4,880,839 A | 11/1989 | Tucker | |
| 5,162,504 A | 11/1992 | Horoszewicz | |
| 5,609,849 A | 3/1997 | Kung | |
| 5,656,651 A | 8/1997 | Sovak et al. | |
| 6,019,957 A | 2/2000 | Miller et al. | |
| 6,071,957 A | 6/2000 | Miller et al. | |
| 6,160,011 A | * 12/2000 | Miller et al. ................ | 514/522 |
| 2001/0012839 A1 | 8/2001 | Miller et al. | |

FOREIGN PATENT DOCUMENTS

| | | |
|---|---|---|
| EP | 0 040 932 | 12/1981 |
| EP | 0 100 172 | 2/1984 |
| WO | WO 95/19770 | 7/1995 |
| WO | WO 98/53826 | 12/1998 |

OTHER PUBLICATIONS

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4–(trifluoromethyl)–2H–pyrano[3,2–g]quinolin–2–one. Bioorg. Med. Chem. Lett., 9: 1003, 1999.

Zhi L, Tegley CM, Marschke KB, and Jones TK. Switching androgen receptor antagonists to agonists by modifying C–ring substituents on piperidino[3,2–g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4–Alkyl– and 3,4–diaklyl–1,2,3, 4–tetrahydro–8–pyridono[5,6–g]quinolines: potent, nonsteroidal androgen receptor agonists. Bioorg. Med. Chem. Lett., 9:1335, 1999.

Hamann LG, Mani NS, Davis RL, Wang XN, Marschke KB, and Jones TK. Discovery of a potent, orally active nonsteroidal androgen receptor agonist: 4–ethyl–1,2,3, 4–tetrahydro–6–(trifluoromethyl)–8–pyridono[5,6–g] quinoline (LG121071). J. Med. Chem., 42: 210, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun.,244(1):1–4, 1998.

Edwards JP, West SJ, Pooley CLF, Marschke KB, Farmer LJ, and Jones TK. New nonsteroidal androgen receptor modulators based on 4–(trifluoromethyl)–2–(1 H)–Pyrololidino[3,2–g]quinolone. Bioorg. Med. Chem. Lett., 8: 745, 1998.

Howard Tucker and Glynne J. Chesterson, J. Med Chem. 1988, 31, pp. 885–887, "Resolution of the Nonsteroidal Antiandrogen—4'–Cyano–3–[(4–fluorophenyl)sulfonyl] 2–methyl–3'–(trifluoromethyl)–propionanilide and the Determination of the Absolute Configuration of the Active Enantiomer".

D. McKillop, et al., "Enantioselective metabolism and pharmacokinetics of Casodex in the male rat", Xenobiotica, 1995, vol. 25, No. 6, 623–634.

Leonid Kirkovsky, et al., "[$^{125}$I]–Radionated Bicalutamide Analogs as Potential Imaging Agents for Prostate Cancer", Poster Presentation MEDI 155, 214th ACS National Meeting, Las Vegas, NV, Sep. 7–11, 1997, Department of Pharmaceutical Sciences, University of Tennessee, Memphis, TN 38163.

U.S. patent application Ser. No. 09/644,970, Dalton et al., filed Aug. 24, 2000.

(List continued on next page.)

*Primary Examiner*—Shailendra Kumar
(74) *Attorney, Agent, or Firm*—Mark S. Cohen; Eitan, Pearl, Latzer & Cohen-Zedek

(57) ABSTRACT

The present invention relates to a novel class of androgen receptor targeting agents (ARTA) which demonstrate androgenic and anabolic activity of a nonsteroidal ligand for the androgen receptor. The agents define a new subclass of compounds which are selective androgen receptor modulators (SARM) which are useful for male hormone therapy such as oral testosterone replacement therapy, treating prostate cancer, imaging prostate cancer.

5 Claims, 9 Drawing Sheets

OTHER PUBLICATIONS

David T. Baird and Anna F. Glasier, "Hormonal Contraception—Drug Therapy", The New England Journal of Medicine, May 27, 1993, pp. 1543–1549.

F.C. W. Wu, "Male Contraception: Current Status and Future Prospects", Clinical Endocrinology, (1988), 29, pp. 443–465.

Carl Djerassi and S.P. Leibo, "A new look at male contraception", Nature. vol. 370, pp. 11–12.

World Health Organisation Task Force on Methods for the Regulation of Male Fertility, "Contraceptive efficacy of testosterone–induced azoospermia in normal men", The Lancet, vol. 336, Oct. 20, 1990, pp. 955–959 and 1517–1518.

C. G. Francisco, et al., "Long–acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76–81.

Leonid Kirkovsky, et al., "Approaches to Irreversible non--steroidal chiral antiandrogens", Department of Pharmaceutical Sciences, University of Tennessee, 47th Southeast/51st Southwest Joint Regional Meeting of the American Chemical Society, Memphis, TN, Nov. 29–Dec. 1, 1995.

David J. Handelsman, "Bridging the gender gap in contraception: another hurdle cleared" The Medical Journal of Australia, vol. 154, Feb. 18, 1996, pp. 230–233.

* cited by examiner

SELECTIVE ANDROGEN RECEPTOR MODULATORS AND METHODS OF USE THEREOF

This application is a Continuation Application of U.S. Ser. No. 09/644,970, filed Aug. 24, 2000, now abandoned, and claims priority of U.S. Ser. No. 60/300,083, filed Jun. 25, 2001, which are hereby incorporated by reference.

FIELD OF INVENTION

The present invention relates to a novel class of androgen receptor targeting agents (ARTA) which demonstrate androgenic and anabolic activity of a nonsteroidal ligand for the androgen receptor. The agents define a new subclass of compounds which are selective androgen receptor modulators (SARM) which are useful for mate hormone therapy such as oral testosterone replacement therapy, treating prostate cancer, imaging prostate cancer.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testis and the cortex of the adrenal gland, or synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857–75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues, DHT is thus thought to serve as the intracellular mediator for most androgen actions (Zhou, et al., Molec. Endocrinol. 9:208–18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199–205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive to devices, historically, society has looked to women to be responsible for contraceptive decisions and their consequences. Although health concerns over sexually transmitted diseases has made men more aware of the need to develop safe and responsible sexual habits, women still often bear the brunt of contraceptive choice. Women have a number of choices from temporary mechanical devices such as sponges and diaphragms to temporary chemical devices such as spermicides. Women also have at their disposal more permanent options such as physical devices like IUDs and cervical caps as well as more permanent chemical treatments such as birth control pills and subcutaneous implants. However, to date, the only options available for men include the use of condoms and a vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long term methods which required no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320–28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods Ar Regulation of Male Fertility, "Contraceptive Efficacy of Testosterone-Induced Azoospermia and Oligospermia in Normal Men," Fertilily and Sterility 65:821–29 (1996)).

A variety of testosterone esters have been developed which are more slowly absorbed after intramuscular injection and, thus, result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626–36 (1996)).

SUMMARY OF THE INVENTION

This invention provides a novel class of androgen receptor targeting agents (ARTA). The agents define a new subclass of compounds which are selective androgen receptor modulators (SARM) which are useful for oral testosterone replacement therapy which have an unexpected in-vivo activity for an androgenic and anabolic activity of a nonsteroidal ligand for the androgen receptor.

The present invention relates to a selective androgen receptor modulator compound having in-vivo androgenic and anabolic activity of a nonsteroidal ligand for the androgen receptor selective androgen receptor modulator compound having the formula (Compound I):

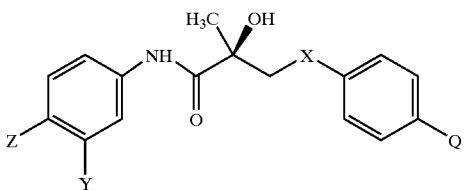

where X is a O, $CH_2$, NH, Se, PR, or NR;
Z is a hydrogen bond acceptor, $NO_2$, CN, COR, CONHR;
Y is a lipid soluble group, I, $CF_3$, Br, Cl, $SnR_3$;
R is an alkyl group or OH; and
Q is acetamido-, trifluroacetamido-, alkylamines, ether, alkyl, N-sulfonyl, O-sulfonyl, alkylsulfonyl, carbonyl, or a ketone.

The present invention relates to a selective androgen receptor modulator compound having in-vivo androgenic and anabolic activity of a nonsteroidal ligand for the androgen receptor selective androgen receptor modulator compound having the formula (Compound II):

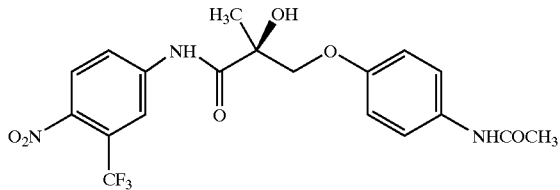

The present invention also relates to a selective androgen receptor modulator compound having in-vivo androgenic and anabolic activity of a nonsteroidal ligand for the androgen receptor having the formula (compound III):

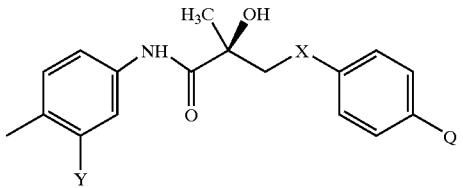

where
X is a O, $CH_2$, NH, Se, PR, or NR;
Z is $NO_2$, CN, COR, or CONHR;
Y is I, $CF_3$, Br, Cl, or $SnR_3$;
R is an alkyl group or OH; and
Q is acetamido or trifluroacetamido.

The present invention also relates to a method of binding a selective androgen receptor modulator compound to a androgen receptor which includes contacting the androgen receptor with the selective androgen receptor modulator compound under conditions effective to bind the selective androgen receptor modulator compound to the androgen receptor.

Another aspect of the present invention relates to a method of suppressing spermatogenesis in a subject which includes contacting an androgen receptor of the subject with a selective androgen receptor modulator compound under conditions effective to suppress spermatogenesis.

The present invention also relates to a method of hormone therapy which comprises administrating to the subject an effective amount of the selective androgen receptor modulator compound. In one embodiment, the selective androgen receptor modulator compound is selective for androgen or testosterone receptor. The present invention also relates to a method of oral administration of the selective androgen receptor modulator compound.

The present invention also relates to a method of hormone therapy which includes contacting an androgen receptor of a patient with a selective androgen receptor modulator compound under conditions effective to bind the selective androgen receptor modulator compound to the androgen receptor and effect a change in an androgen-dependent condition.

The present invention also relates to composition and a pharmaceutical composition which comprises a selective androgen receptor modulator and a suitable carrier or diluent.

Still another aspect of the present relates to a method of producing a selective androgen receptor modulator or a non-steroidal AR agonist compound of the present invention.

The novel selective androgen receptor modulator compounds of the present invention, either alone or as a composition, are useful as a male contraceptive or in the treatment of a variety of hormone-related conditions, such as hypogonadism, sarcopenia, erythropoiesis, and osteoporesis. Further, the selective androgen receptor modulator compounds are useful for oral testosterone replacement therapy.

The selective androgen receptor modulator compounds of the present invention offer a significant advance over steroidal androgen treatment because the selective androgen receptor modulator compounds of the present invention have been shown in-vivo to have an androgenic and anabolic activity of a nonsteroidal ligand for the androgen receptor. Thus, the selective androgen receptor modulator compounds have an androgenic and anabolic activity of a nonsteroidal ligand for the androgen receptor and will not be accompanied by serious side effects, inconvenient modes of administration, or high costs and still have the advantages of oral bioavailability, lack of cross-reactivity with other steroid receptors, and long biological half-lives.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1:
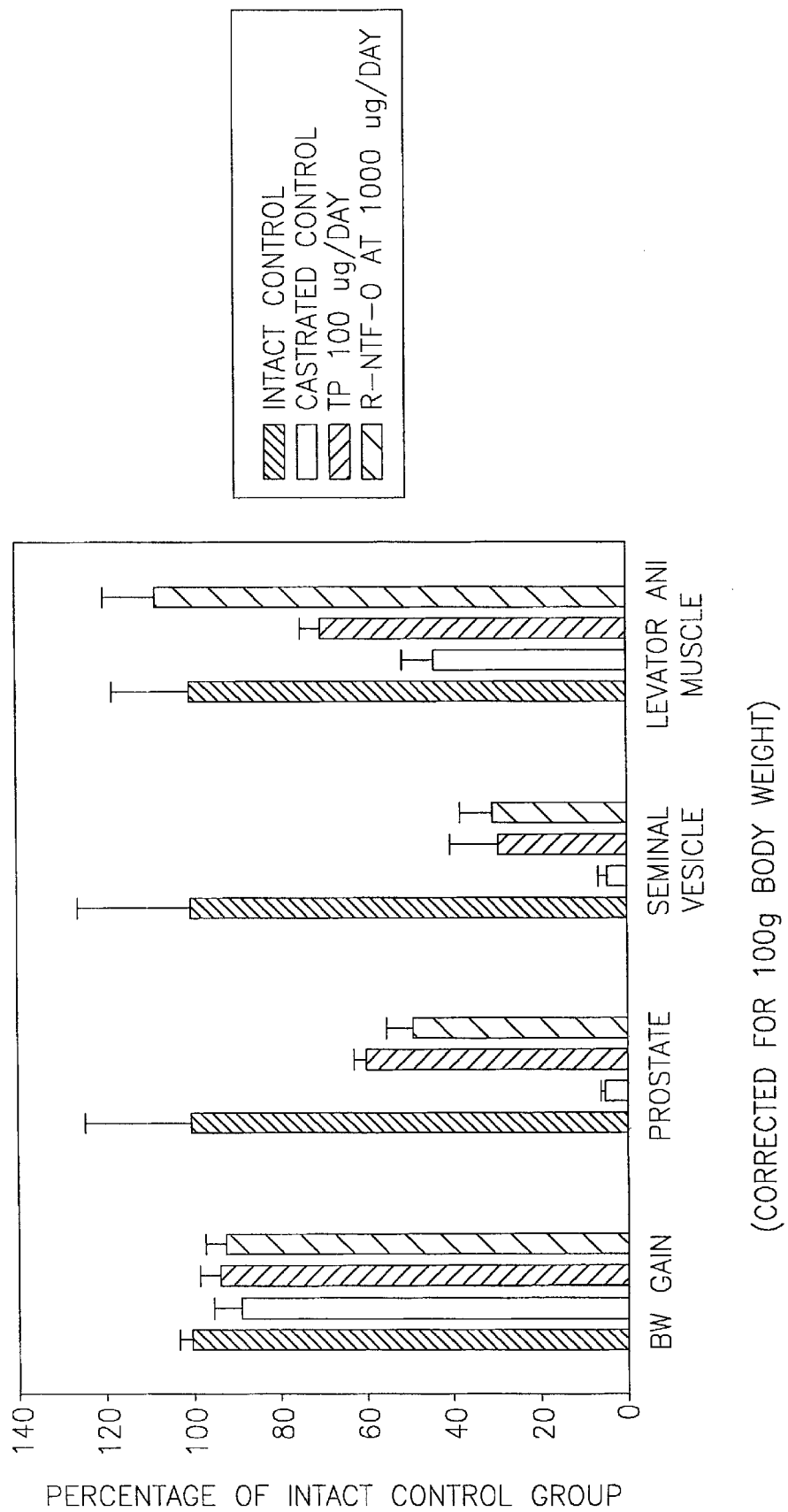
FIG. 1: Androgenic and Anabolic activity of (S)-GTx-007 in rats. Rats were left untreated (intact control), castrated (castrated control), treated with testosterone propionate (TP), or treated with S-GTx-007, and the body weight gain as well as the weight of androgen-responsive tissues (prostate, semimal vesicles and levator ani muscle) was determined.

This invention provides a novel class of androgen receptor targeting agents (ARTA). The agents define a new subclass of compounds which are selective androgen receptor modulators (SARM) which are useful for oral testosterone replacement therapy which have an unexpected in-vivo activity for an androgenic and anabolic activity of a nonsteroidal ligand for the androgen receptor. Furthers these compounds are effective to treat prostate cancer and useful for imaging of prostate cancer. As demonstrated herein, the compounds demonstrate an in-vivo androgenic and anabolic activity of a nonsteroidal ligand for the androgen receptor.

The present invention relates to a selective androgen receptor modulator compound having in-vivo androgenic and anabolic activity of a nonsteroidal ligand for the androgen receptor selective androgen receptor modulator compound having the formula:

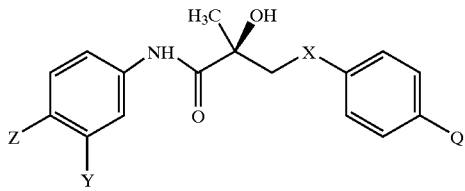

where

X is a O, CH$_2$, NH, Se, PR, or NR;

Z is a hydrogen bond acceptor, NO$_2$, CN, COR, CONHR;

Y is a lipid soluble group, I, CF$_3$, Br, Cl, SnR$_3$;

R is an alkyl group or OH; and

Q is acetamido-, trifluroacetamido-, alkylamines, ether, alkyl, N-sulfonyl, O-sulfonyl, alkylsulfonyl, carbonyl, or a ketone.

In one embodiment X of the selective androgen receptor modulator compound is O. In another embodiment Z is NO$_2$. In another embodiment Y is CF$_3$. In another embodiment Q is NHCOCH$_3$.

The present invention also relates to a selective androgen receptor modulator compound having in-vivo androgenic and anabolic activity of a nonsteroidal ligand for the androgen receptor selective androgen receptor modulator compound having the formula:

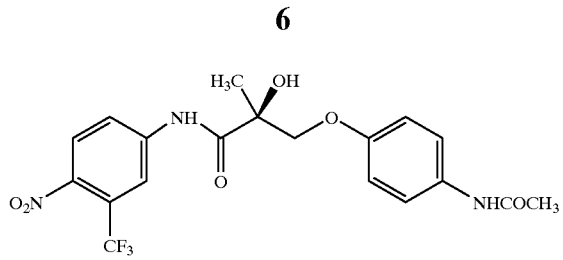

The present invention also relates to a selective androgen receptor modulator compound having in-vivo androgenic and anabolic activity of a nonsteroidal ligand for the androgen receptor having the formula:

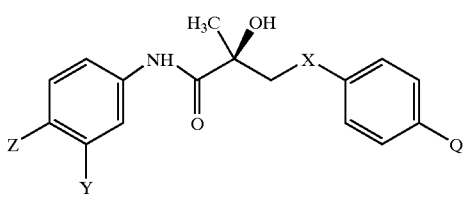

where

X is a O, CH$_2$, NH, Se, PR, or NR;

Z is NO$_2$, CN, COR, or CONHR;

Y is I, CF$_3$, Br, Cl, or SnR$_3$;

R is an alkyl group or OH; and

Q is acetamido or trifluroacetamido.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glueocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration.

The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists).

The present invention is directed to selective androgen receptor modulator compounds which are agonist compounds, and are, therefore, useful in binding to and activating steroidal hormone receptors. The compounds are non-steroidal. Preferably, the agonist compound of the present invention is an agonist which binds the androgen receptor. Preferably, the compound has high affinity for the androgen receptor. The compound may bind either reversibly or irreversibly to the androgen receptor. The compound of the present invention may contain a functional group (affinity label) that allows alkylation of the androgen receptor (i.e. covalent bond formation). Thus, in this case, the compound binds irreversibly to the receptor and, accordingly, cannot be displaced by a steroid, such as the endogenous ligands dihydrotestosterone and testosterone. It is preferable, however, for the compounds of the present invention reversibly to bind the androgen receptor.

The compounds of the present invention include racemic mixtures of the R and S enantiomers. Preferred are substantially pure R and S enantiomers of the compounds "Substantially pure" is defined herein as greater than about 95% preponderance of one isomer. Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution According to one aspect of the present invention, a method is provided for binding the selective androgen receptor modulator compounds of the present invention to an androgen receptor by contacting the receptor with a selective androgen receptor modulator compound under conditions effective to cause the selective androgen receptor modulator compound to bind the androgen receptor. The binding of the selective androgen receptor modulator compounds to the androgen receptor enables the compounds of the present invention to be useful as a male contraceptive and in a number of hormone therapies. The agonist compounds bind to and activate the androgen receptor. Binding of the agonist compound is either reversible or irreversible, preferably reversible.

According to one aspect of the present invention, a method is provided for suppressing spermatogenesis by contacting an androgen receptor of a patient with a selective androgen receptor modulator compound under conditions effective to bind the selective androgen receptor modulator compound to the androgen receptor and suppress spermatogenesis.

According to another aspect of the present invention, a method is provided for hormonal therapy in a patient (i.e., suffering from an androgen-dependent condition) which includes contacting an androgen receptor of a patient with a selective androgen receptor modulator compound under conditions effective to bind the selective androgen receptor modulator compound to the androgen receptor and effect a change in an androgen-dependent condition. Androgen-dependent conditions which may be treated according to the present invention include those conditions which are associated with aging, such as hypogonadism, sarcopenia, erythropoiesis, osteoporosis, and any other conditions later determined to be dependent upon low androgen (e.g., testosterone) levels.

As used herein, "pharmaceutical composition" means therapeutically effective amounts of the SARM together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or Lyophilized or otherwise dried formulations and include diluents of various buffer content (e.g., Tris-HCI., acetate, phosphate), pH and ionic strength, additives such as albumin or gelatin to prevent absorption to surfaces, detergents (e.g., Tween 20, Tween 80, Pluronic F68, bile acid salts), solubilizing agents (e-g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance, Controlled or sustained release compositions include formulation in lipophilic depots (e.g., fatty acids, waxes, oils).

Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g, fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment a controlled release system can be placed in proximity of the therapeutic target, i.e., the brain, thus requiring only a fraction of the systemic dose (see, e.g, Goodson, in Medical Applications of Controlled Release, supra, vol. 2, pp. 115–138 (1984). Preferably, a controlled release device is introduced into a subject in proximity of the site of inappropriate immune activation or a tumor. Other controlled release systems are discussed in the review by Langer (Science 249:1527–1533 (1990).

The pharmaceutical preparation can comprise the chernopreventive agent alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the chernopreventive agent can be administered to a subject by, for example, subcutaneous implantation of a pellet; in a further embodiment, the pellet provides for controlled release of chernopreventive agent over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the chernopreventive agents or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the SARM agents or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the SARM agents or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527–1533 (1990); Treat et al., in Liposomes in the Therapy of Infectious Disease and Cancer, Lopez- Berestein and Fidler (eds.), Liss, N.Y., pp. 353–365 (1989); Lopez-Berestein, ibid., pp. 317–327; see generally ibid).

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acids fumaric acid, maleic acid, succinic acid, acetic acid, benzoic: acid, oxalic acid, citric acid, tartaric acid, carbonic acid or phosphoric acid.

The following examples are presented in order to more fully illustrate the preferred embodiments of the invention. They should in no way be construed, however, as limiting the broad scope of the invention.

Experimental Details Section

Nonsteroidal Ligands with Androgenic and Anabolic Activity

The SARM compounds provided herein were designed, synthesized and evaluated for in-vitro and it-vivo pharmacologic activity. The in-vitro androgen receptor binding affinity and ability to maintain androgen dependent tissue growth in castrated animals was studied. Androgenic activity was monitored as the ability of the SARM compounds to maintain and/or stimulate the growth of the prostate and seminal vesicles, as measured by weight. Anabolic activity was monitored as the ability of the SARM compounds to maintain and/or stimulate the growth of the levator ani muscle, as measured by weight.

Synthetic Procedures of Compounds (2R)1-Methacryloylpyrrolidin-2-carboxylic Acid (R-129). D-Proline (R-128, 14.93 g, 0.13 mol) was dissolved in 71 mL of 2 N NaOH and cooled in an ice bath; the resulting alkaline solution was diluted with acetone, (71 mL). An acetone solution (71 mL) of metacryloly chloride 127 (13.56 g, 0.13 mol) and 2N NaOH solution (71 mL) were simultaneously added over 40 min to the aqueous solution of D-proline in an ice bath. The pH of the mixture was kept at 10–11° C. during the addition of the metacryloly chloride. After stirring (3 h, room temperature), the mixture was evaporated in vacuo at a temperature at 35–45° C. to remove acetone The resulting solution was washed with ethyl ether and was acidified to pH 2 with concentrated HCl . The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexNdes afforded 16.2 (68%) of the desired compound as colorless crystals: mp 102–103° C. (lit. [214] mp 102.5–103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48–4.44 for the first rotamer, 4.24–4.20 (m) for the second rotamer (totally 1H for both rotamers, CH at the chiral canter), 3.57–3.38 (m, 2H, $CH_2$), 2.27–2.12 (1H, CH), 1.97–1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; [α]$D^{26}$+80.8°(c=1, MeOH); Anal. Calcd. for $C_9H_{13}NO_3$: C 59.00, H 7.15, N 7.65. Found: C 59.13, H 7.19, N 7.61.

(3R,8aR)-3-Bromomethyl-3-methyl-tetrahydro-pyrrolo[2,1-c][1,4]oxazine-1,4dione (R, R-130). A solution of NBS (23.5 g, 0.132 mol) in 100 mL of DMF was added dropwise to a stirred solution of compound R-129 (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152–154° C. (lit. [214] mp 107–109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$) 3.86 (d, J=11.4 Hz, 1H, $CHH_b$), 3.53–3.24 (m, 4H, $CH_2$), 2.30–2.20 (m, 1H, CH), 2.04–1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$D^{26}$=124.5° (c=1.3, chloroform); Anal. Calcd. for $C_9H_{12}BrNO_3$: C 41.24 H 4.61, N 5.34. Found: C41.46, H 4.64, N 5.32.

(2R3Bromo2-hydroxy-2-methylpropanoic Acid (R-131). A mixture of bromolactone R-130 (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH-1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107–109° C. (lit. [214] mp 109–113° C. for the S-isomer); $_1$H NMR (300 MHz, DMSO-$d_6$) δ 6 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300–2500 (COOH), 1730 (C=O ), 1449, 1421, 1380, 1292, 1193, 1085 cm$^{-1}$; [α]$D^{26}$+10.5° (c=2.6, MeOH); Anal. Calcd for $C_4H_7BrO_3$: C 26.25, H 3.86. Found: C 26.28, H 3.75.

N-[4-Nitro-3(trifluoromethyl)phenyl]-(2R)-3-bromo-2-hydroxy-2-methylpropanamide (R-132). Thionyl chloride (8.6 g, 72 mmol) was added dropwise under argon to a solution of bromoacid R-131 (11.0 g, 60 mmol) in 70 mL of DMA at −5 to −10° C. The resulting mixture was stirred for 2 h under the same conditions. A solution of 4-nitro-3-trifluoromethyl-aniline (12.4 g, 60 mmol) in 80 mL of DMA was added dropwise to the above solution, and the resulting mixture was stirred overnight at room temperature. The solvent was removed on Rotavapor using high vacuum oil pump; the residue was diluted with saturated $NaHCO_3$ solution, and extracted with ethyl ether (100 mL×3). Combined extracts were dried over anhydrous $Na_2SO_4$, filtered through Celite, and purified by flash chromatography on silica gel, using methylene chloride as eluent to afford 18.0 g (80%) of the desired compound: mp 98–100° C. ($R_f$=0.2, silica gel, $CH_2Cl_2$); $^1$H NMR (300 MHz, DMSO-$d_6$) δ 10.54 (s, 1H, NH), 8.54 (d, J=2.1 Hz, 1H, ArH), 8.34 (dd, J=9.0 Hz, J=2.1 Hz, 1H, ArH), 8.18 (d, J=9.0 Hz, 1H1, ArH), 6.37 (s, 1H, OH), 3.82 (d, J=10.4 Hz, 1H, $CHH_a$), 3.58 (d, J=10.4 Hz, 1H, $CHH_b$ ), 1.48 (s, 3H, Me); $^{13}$C NMR (75 MHz, DMSO-$d_6$) δ 173.6 (C=O), 143.0, 127.2, 123.2, 122.6 (q, J=33.0 Hz), 122.0 (q, J=271.5 Hz), 118.3 (q, J=6.0 Hz), 74.4, 41,4, 24.9; IR (KBr) 3344 (OH), 1680 (C=O), 1599, 1548 (C=C, Ar), 1427, 1363, 1161 cm$^{-1}$; MS (ESI): m/z 370.8 (M)$^+$; Anal. Calcd. for $C_{11}H_{10}BrN_2O_4$: C 35.60, H 2 72, N 7.55, Found: C 35.68, H 2.72, N 7.49.

N-[4nitro-3-trifluoromethyl)phenyl]-(2S)-3-[4-(acetylamino)phenoxy]-2-hydroxy-2-methylpropanamide (S-147). The title compound was prepared from compound R-132 (0.37 g, 1.0 mmol), 4-acetamidophenol (0.23 g, 1.5 mmol) K$_2$CO$_3$ (0.28 g, 2.0 mmol), and 10% of benzyltributylammonium chloride as a phase transfer catalyst in 20 mL of methyl ethyl ketone was heated at reflux overnight under argon. The reaction was followed by TLC, the resulting mixture was filtered through Celite, and concentrated in vacuo to dryness. Purification by flash column chromatography on silica gel (hexanes-ethyl acetate, 3:1) yielded 0.38 g (86%) (R$_f$=0.18 hexanes-ethyl acetate, 3:1) of the desired compound as a light yellow powder: mp 70–74° C.; The solid can be recrystalized from ethyl acetate and hexane), $^1$H NMR (300 MHz, DMSO-d$_6$) δ 10.62 (s, 1H, NH), 9.75 (s, 1H, NH), 8.56 (d, J=1.9 Hz, 1H, ArH), 8.36 (dd, J=9.1 Hz, J=1.9 Hz, 1H, ArH), 8.18 (d, J=9.1 Hz, 1H, ArH), 7.45–7.42 (m, 2H, ArH), 6.85–6.82 (m, 2H, ArH), 6.25 (s, 1H, OH), 4.17 (d, J=9.5 Hz, 1H, CHH$_a$), 3.94 (d, J=9.5 Hz, 1H, CHH$_b$), 1.98 (s, 3H, Me), 1.43 (s, 3H, Me); $^{13}$C NMR (75 MHz, DMSO-d$_6$) δ 174.6 (C=O), 167.7, 154.2, 143.3, 141.6, 132.8, 127.4, 123.0, 122.7 (q, J=33.0 Hz), 122.1 (q, J=271.5 Hz), 120.1, 118.3 (q, J=6.0 Hz), 114.6, 74.9, 73.8, 23.8, 23.0; IR (KBr) 3364 (OH), 1668 (C=O), 1599, 1512 (C=C,Ar), 1457, 1415, 1351, 1323, 1239, 1150 1046 cm$^{-1}$; MS (ESI): m/z 464.1 (M+Na)$^+$; Anal. Calcd. for C$_{19}$H$_{18}$F$_3$N$_3$O$_6$: C 51.71, H 4.11, N 9.52. Found: C 52.33, H 4.40, N 9.01.

The in-vitro activity of the SARM compounds, specifically compound VII, demonstrated high androgen receptor binding affinity (Ki=7.5 nM). Animal studies with the SARM compounds, specifically compound V, demonstrated that it is a potent androgenic and anabolic nonsteroidal agent. Four groups of rats were used for these studies: (1) intact controls, (2) castrated controls, (3) castrated animals treated with testosterone propionate (100 μg/day), and (4) castrated animals treated with compound V (1000 μg/day). Testosterone and compound VII were delivered at a constant rate for 14 days via subcutaneous osmotic pumps.

The results of these studies are shown in FIG. 1. Castration significantly reduced the weight of androgenic (e.g., prostate and seminal vesicles) and anabolic (e.g., levator ani muscle) tissues, but had little effect on animal body weight (BW). Treatment of castrated animals with testosterone propionate or compound VII maintained the weight of androgenic tissues to the sane degree. Compound VII had similar androgenic activity as testosterone propionate (i.e., the prostate and seminal vesicle weights were the same), but much greater efficacy as an anabolic agent Compound VII showed greater anabolic activity than testosterone propionate at the doses tested (i.e., the levator ani muscle maintained the same weight as intact control animals and was greater than that observed for testosterone). The experiments presented herein are the first in-vivo results which demonstrate tissue-selective androgenic and anabolic activity (i.e., differing androgenic and anabolic potency) of a nonsteroidal ligand for the androgen receptor.

EXAMPLE 2

The in-vivo efficacy and acute toxicity of four novel nonsteroidal androgens (compounds IV, V, VI and VII) in rats was examined. In-vitro assays established that these compounds bind the androgen receptor with very high affinity. The structures and names of the four compounds are presented below:

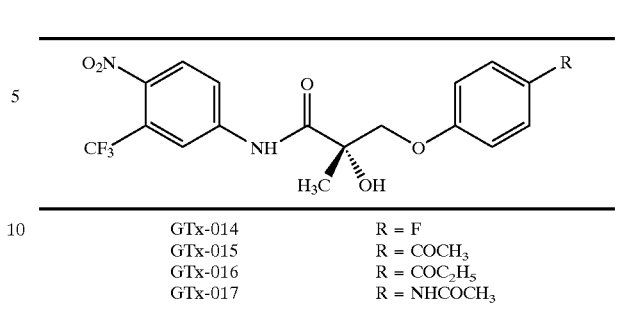

| | |
|---|---|
| GTx-014 | R = F |
| GTx-015 | R = COCH$_3$ |
| GTx-016 | R = COC$_2$H$_5$ |
| GTx-017 | R = NHCOCH$_3$ |

Experimental Methods

Figure 9:
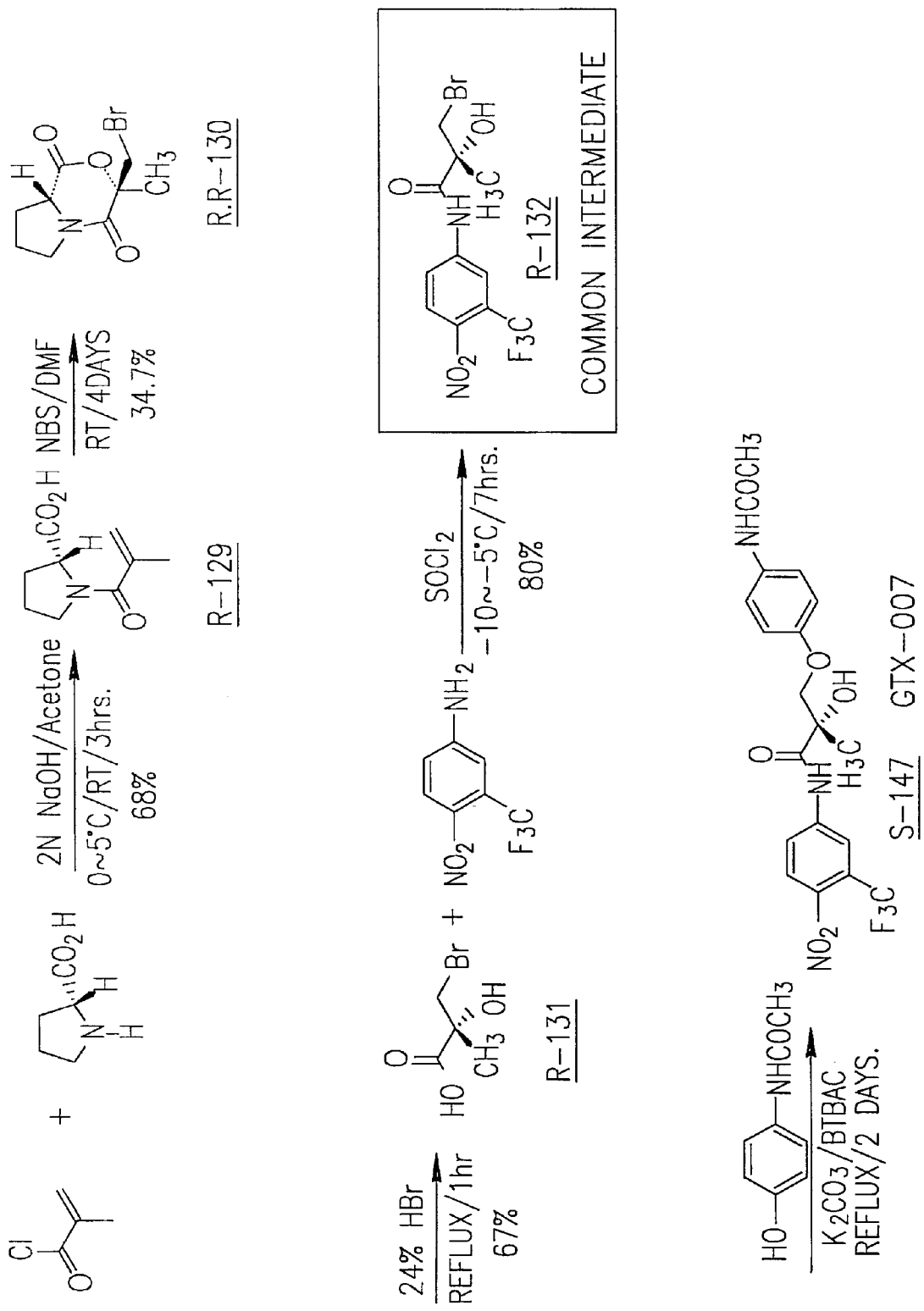
FIG. 9: Synthesis scheme of GTX-007.

Materials. The S-isomers of compounds GTx-014 (compound IV), GTx-015 (compound V), GTx-016 (compound VI) and GTx-007 (compound VII wherein R is NHCOCH3) was synthesized in accordance with the scheme as set forth in FIG. 9. Testosterone propionate (TP), polyethylene glycol 300 (PEG300, reagent grade) and neutral buffered formalin (10% w/v) were purchased from Sigma Chemical Company (St Louis, Mo.). Alzet osmotic pumps (model 2002) were purchased from Alza Corp. (Palo Alto, Calif.).

Animals. Immature male Sprague-Dawley rats, weighing 90 to 100 g, were purchased from Harlan Biosciences (Indianapolis, In.). The animals were maintained on a 12-hour light-dark cycle with food and water available ad libitum. The animal protocol was reviewed and approved by the Institutional Laboratory Animal Care and Use Committee.

Study Design. Rats were randomly distributed into twenty-nine (29) groups, with 5 animals per group Treatment groups are described in Table 1. One day prior to the start of drug treatment, animals in groups 2 through 29 were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the site cleaned with betadine. The animals were allowed to recover on a sterile pad (until able to stand) and then returned to their cage.

Twenty-four hours later, animals in groups 2 through 29 were re-anesthetized with ketamine/xylazine, and an Alzet osmotic pump(s) (model 2002) was placed subcutaneously in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment (designated in Table 1) dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at −20° C. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Results

The androgenic and anabolic activities the S isomers of compounds GTx-014, GTx015, GTx-016 and GTx-007, and the R isomer of GTx-014 were examined in a castrated rat model after 14 days of administration. Testosterone propionate, at increasing doses, was used as the positive control of anabolic and androgenic effects.

Figure 2:
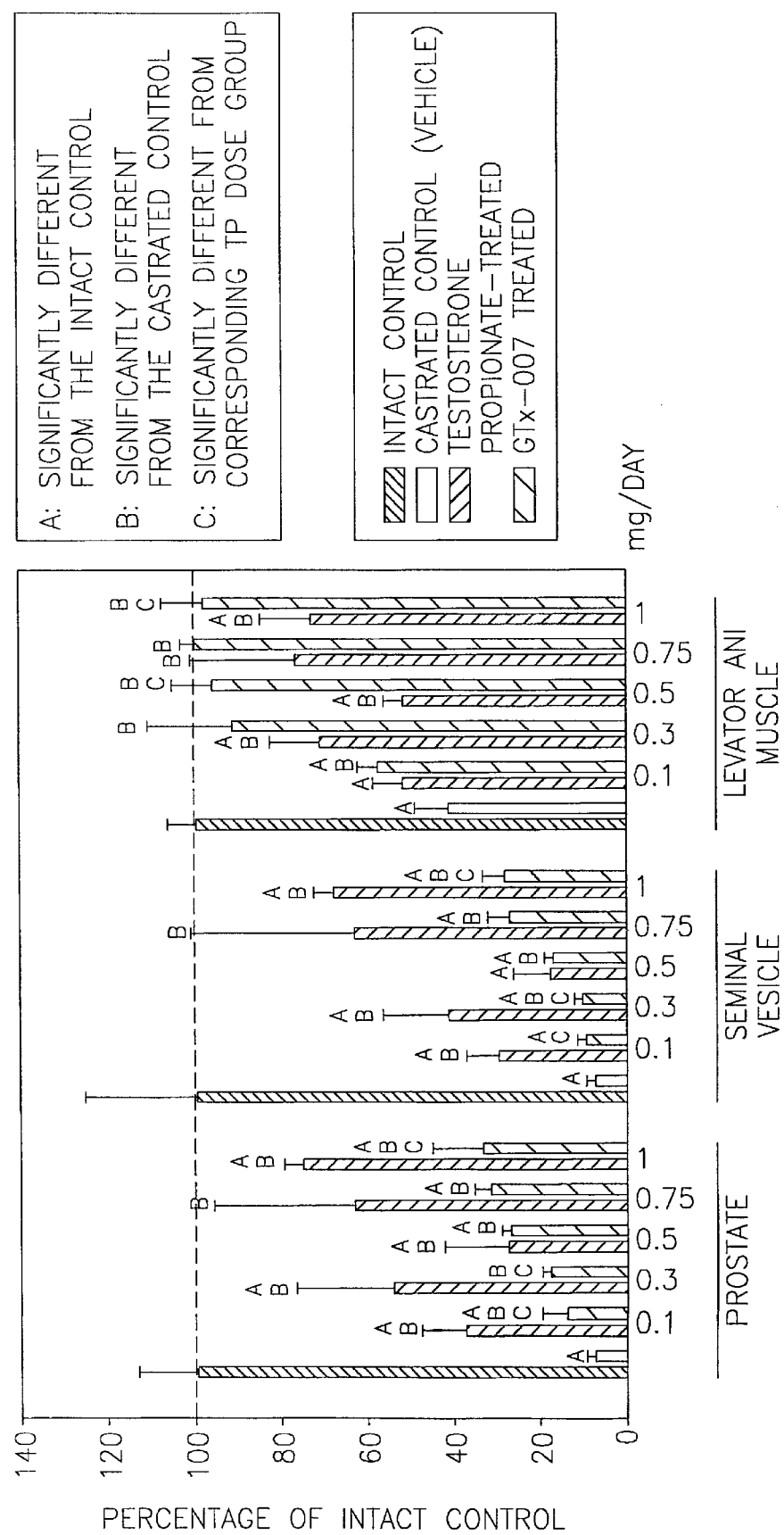
FIG. 2: Androgenic and Anabolic activity of S-GTx-007 in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day S-GTx-007, and the weight of androgen-responsive tissues (prostate, semimal vesicles and levator ani muscle) was determined.
Figure 3:
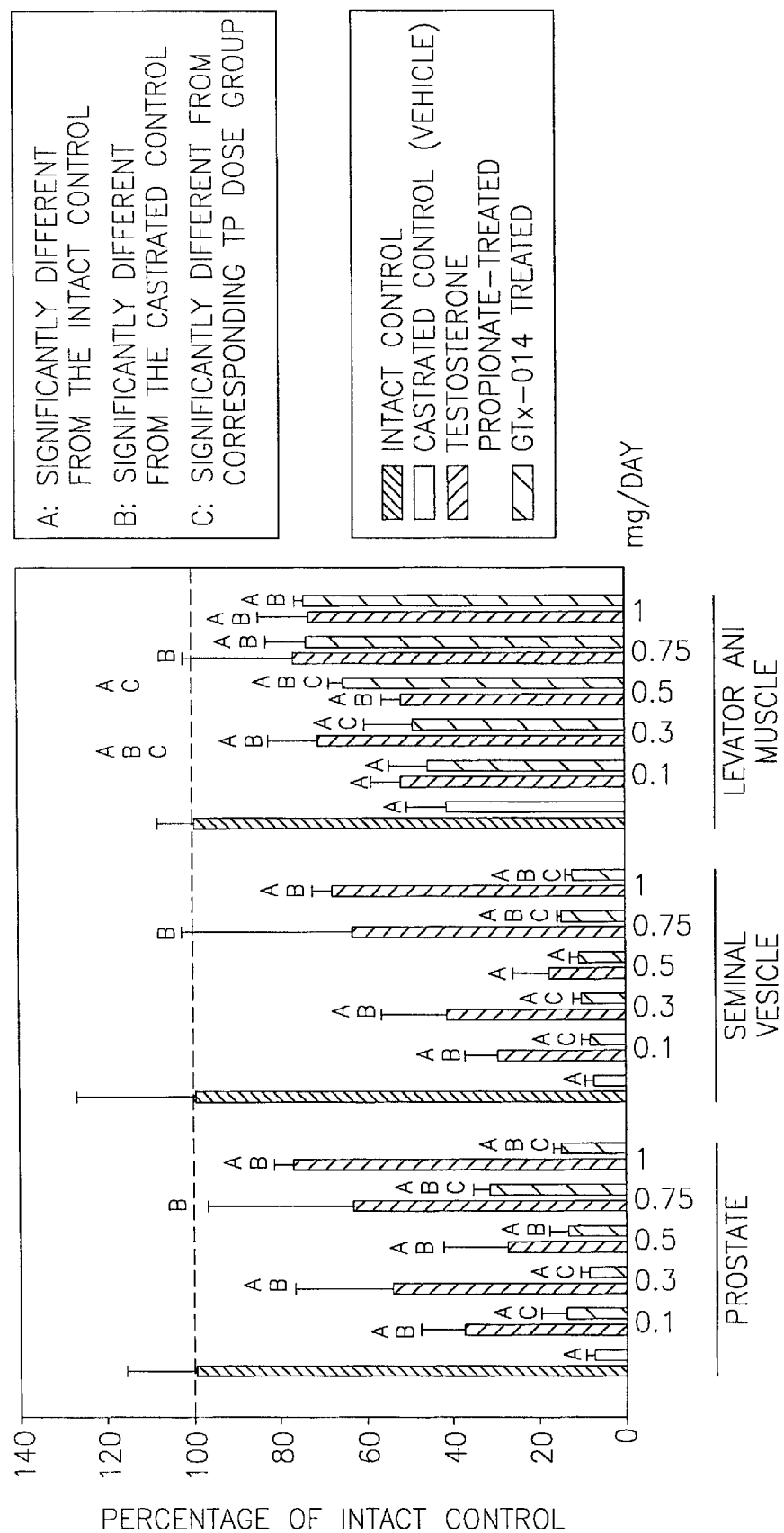
FIG. 3: Androgenic and Anabolic activity of S-GTx-014 in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day S-GTx-014, and the weight of androgen-responsive tissues (prostate, semimal vesicles and levator ani muscle) was determined.

As shown in FIGS. 2 and 3, the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator ani muscle in castrated rats in a dose-dependent manner. The R-isomer of GTx-014, and S-isomers of GTx-015 and GTx-016 showed no effect on the weights of prostate, seminal vesicle, and levator ani muscle in castrated animals (data not shown) The S-isomers of GTx-007 (FIG. 2: S-Gx-007) and GTx-014 (FIG. 3: S-GTx-014) resulted in dose-dependent increases in prostate, seminal vesicle and levator ani muscle weights. Compared with testosterone propionate, S-GTx-007 showed lower potency and intrinsic activity in increasing the weights of prostate and seminal vesicle, but a greater potency and intrinsic activity in increasing the weight of levator ani muscle. Particularly, S-GTx-007, at a dose as low as 0.3 mg/day, was able to maintain the levator ani muscle weight of castrated animals in the same level as that of intact animals. Thus, S-GTx-007 is a potent nonsteroidal anabolic agent with less androgenic activity but more anabolic activity than testosterone propionate. This is a significant improvement over previous claims, in that this compound selectively stimulates muscle growth and other anabolic effects while having less effect on the prostate and seminal vesicles. This may be particularly relevant in aging men with concerns related to the development or progression of prostate cancer.

GTx-014 was less potent than GTx-007, but showed greater tissue selectivity (compare effects on the prostate and seminal vesicles in FIGS. 2 and 3). GTx-014 significantly increased levator ani muscle weights, but showed little to no ability to stimulate prostate and seminal vesicle growth (i.e., the prostate and seminal vesicle weights were less than 20% of that observed in intact animals or in animals treated with testosterone propionate)

Results showed that none of the examined compounds produced significant effect on body weight or the weights of other organs (i.e., liver, kidneys, spleen, lungs and heart). Nor did any compound produce any signs of acute toxicity, as gauged by diagnostic hematology tests and visual examination of animals receiving treatments. Importantly, GTx-007 did not suppress the production of luteinizing hormone (LH) or follicle stimulating hormone (FSH) at a dose of 0.3 mg/day (i.e, a dose that exhibited maximal anabolic effects).

In summary, S-GTx-007 exhibited exceptional anabolic activity in animals by maintaining the weight of levator ani muscle after removal of endogenous androgen. This discovery represents major progress towards the development of therapeutically useful nonsteroidal androgens, and a major improvement (i.e., tissue selectivity and potency) over previous drugs in this class. S-GTx-014 and S-GTx-007 showed selective anabolic activity in comparison with testosterone propionate, an androgenic and anabolic steroid. The tissue-selective activity is actually one of the advantages of nonsteroidal androgens in terms of anabolic-related applications.

Despite similarities in structure and in-vitro functional activity, the S-isomers of compounds GTx-014, GTx-015, GTx-016, and GTx-007 exhibited profound differences in terms of their in-vivo activity. GTx-007 the most efficacious androgenic and anabolic activity in animals, with the anabolic activity greater than that of testosterone propionate. GTx-014 showed a small degree of androgenic activity, but an anabolic activity comparable to testosterone propionate. In contrast, GTx-015 and GTx-016 failed to produce any androgenic or anabolic activity in-vivo.

These studies show the discovery of two members (GTx-014 and GTx-007, compounds, compounds II and V respectively) of a new class of selective androgen receptor modulators (SARMS) that demonstrate potent anabolic effects (e.g., muscle growth) with less androgenic activity (e.g., prostatic growth). This new class of drugs has several advantages over nonselective androgens, including potential therapeutic applications in males and females for modulation of fertility, erythropoiesis, osteoporosis, sexual libido and in men with or at high risk for prostate cancer.

Figure 7:
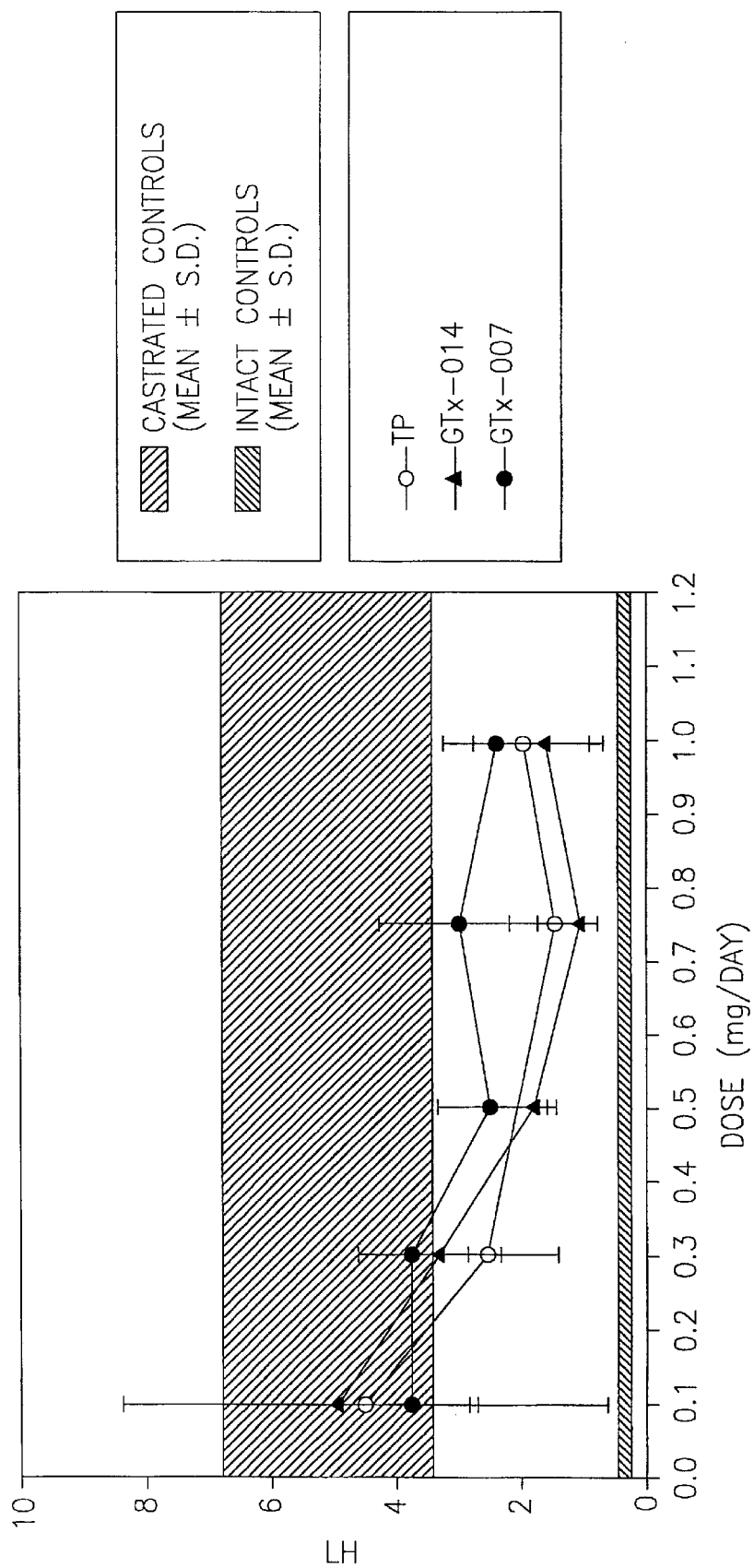
FIG. 7: Effects of GTx-014 and GTx-007 on LH Levels.
Figure 8:
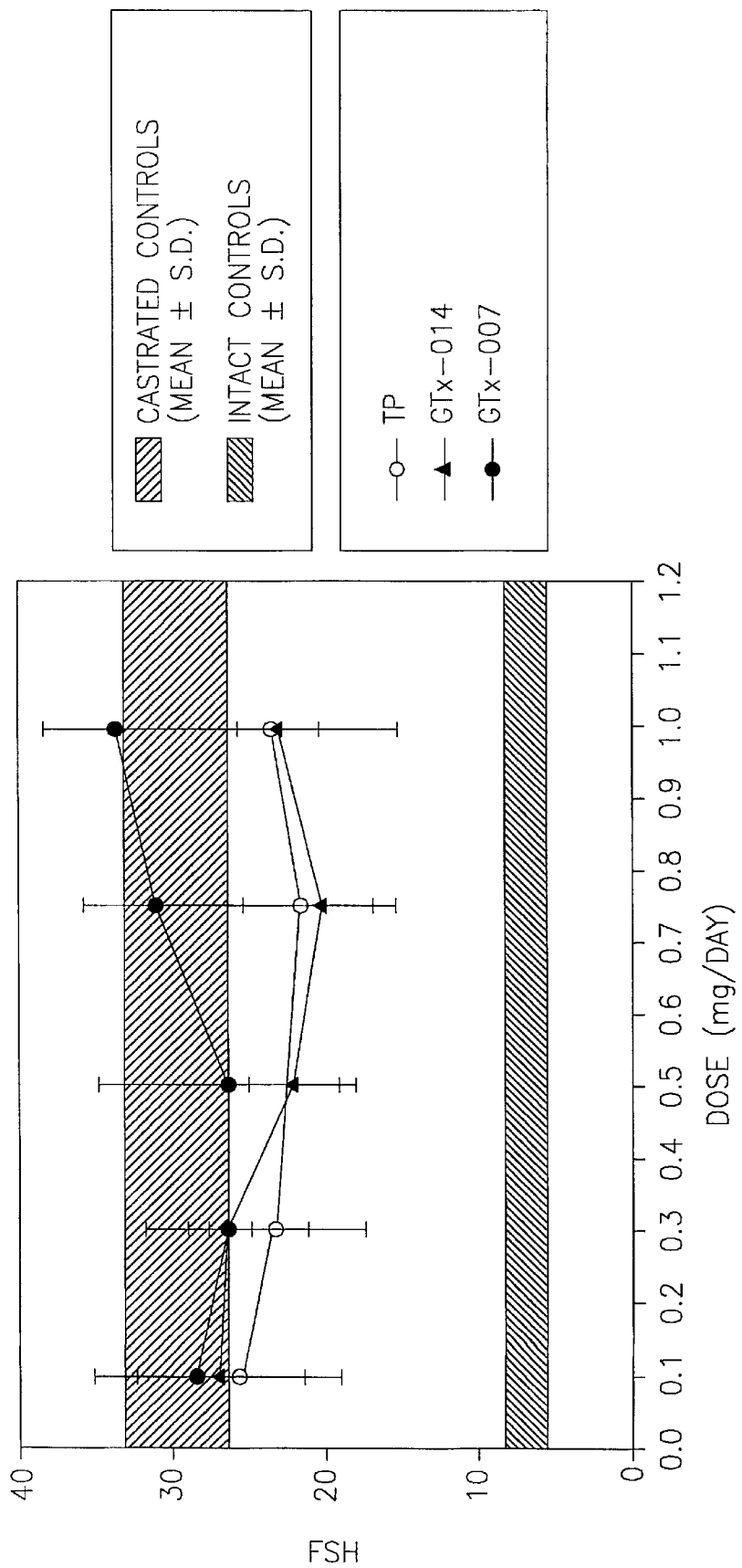
FIG. 8: Effects of GTx-014 and GTx-007 on FSH Levels.

Further, FIGS. 7 and 8 demonstrate the effects of GTx-014 and GTx007 on LH and FSH levels in rats. These results further demonstrate the novelty of these SARMs, due to their differential effects on these reproductive hormones, thus demonstrating the tissue-specific pharmacologic activity. In FIG. 7, LH levels in castrated animals treated with TP and OTx-014 were significantly lower than those of untreated animals (i.e., castrated controls) at doses greater than or equal to 0.3 mg/day. However, higher doses (i.e., 0.5 mg/day or higher) of GTx-007 were required before significant decreases in LH levels were observed. Thus, GTx-007 does not suppress LH levels at doses that are capable of eliciting maximal stimulation of levator ani muscle growth. In FIG. 8, PSH levels in castrated animals treated with GTx-014 were significantly lower than those of untreated animals (i.e., castrated controls) at doses of 0.5 mg/day or higher. Similarly, lower FSH levels were observed in animals treated with TP. However, only this difference was only significant at a dose of 0.75 mg/day. FSH levels in animals treated with GTx-007 were not significantly different from those of untreated animals at any dose level tested. Thus, GTx-007 does not suppress FSH levels at doses that are capable of eliciting maximal stimulation of levator ani muscle growth.

TABLE 1

Animals Groups and Experimental Design

| Group # | Castrated? | Drug | Dose | # of animals |
|---|---|---|---|---|
| 1 | No | None | None | 5 |
| 2 | Yes | None | Vehicle only | 5 |
| 3 | Yes | Testosterone | 0.1 mg/day | 5 |
| 4 | Yes | Testosterone | 0.3 mg/day | 5 |
| 5 | Yes | Testosterone | 0.5 mg/day | 5 |

TABLE 1-continued

Animals Groups and Experimental Design

| Group # | Castrated? | Drug | Dose | # of animals |
|---|---|---|---|---|
| 6 | Yes | Testosterone | 0.75 mg/day | 5 |
| 7 | Yes | Testosterone | 1.0 mg/day | 5 |
| 8 | Yes | R-GTx-014 | 1.0 mg/day | 5 |
| 9 | Yes | S-GTx-014 | 0.1 mg/day | 5 |
| 10 | Yes | S-GTx-014 | 0.3 mg/day | 5 |
| 11 | Yes | S-GTx-014 | 0.5 mg/day | 5 |
| 12 | Yes | S-GTx-014 | 0.75 mg/day | 5 |
| 13 | Yes | S-GTx-014 | 1.0 mg/day | 5 |
| 14 | Yes | S-GTx-015 | 0.1 mg/day | 5 |
| 15 | Yes | S-GTx-015 | 0.3 mg/day | 5 |
| 16 | Yes | S-GTx-015 | 0.5 mg/day | 5 |
| 17 | Yes | S-GTx-015 | 0.75 mg/day | 5 |
| 18 | Yes | S-GTx-015 | 1.0 mg/day | 5 |
| 19 | Yes | S-GTx-016 | 0.1 mg/day | 5 |
| 20 | Yes | S-GTx-016 | 0.3 mg/day | 5 |
| 21 | Yes | S-GTx-016 | 0.5 mg/day | 5 |
| 22 | Yes | S-GTx-016 | 0.75 mg/day | 5 |
| 23 | Yes | S-GTx-016 | 1.0 mg/day | 5 |
| 24 | Yes | S-GTx-007 | 0.1 mg/day | 5 |
| 25 | Yes | S-GTx-007 | 0.3 mg/day | 5 |
| 26 | Yes | S-GTx-007 | 0.5 mg/day | 5 |
| 27 | Yes | S-GTx-007 | 0.75 mg/day | 5 |
| 28 | Yes | S-GTx-007 | 1.0 mg/day | 5 |
| 29 | Yes | None | Vehicle only | 5 |

EXAMPLE 3
Pharmacokinetics of GTx-007 in Dogs

Figure 4:
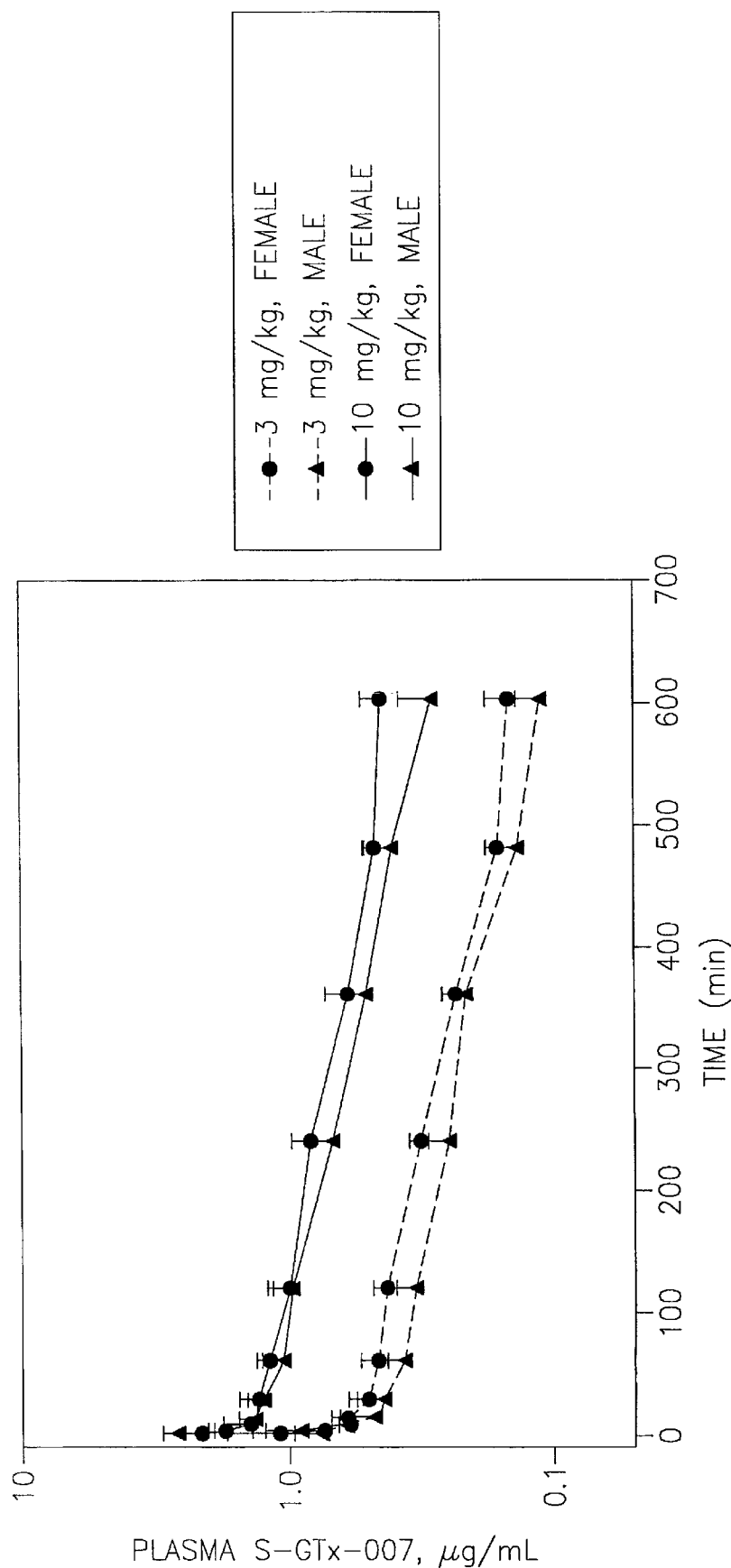
FIG. 4: Average plasma concentration-time profiles of S-GTx-007 in beagle dogs after IV administration at 3 and 10 mg/kg.
Figure 5:
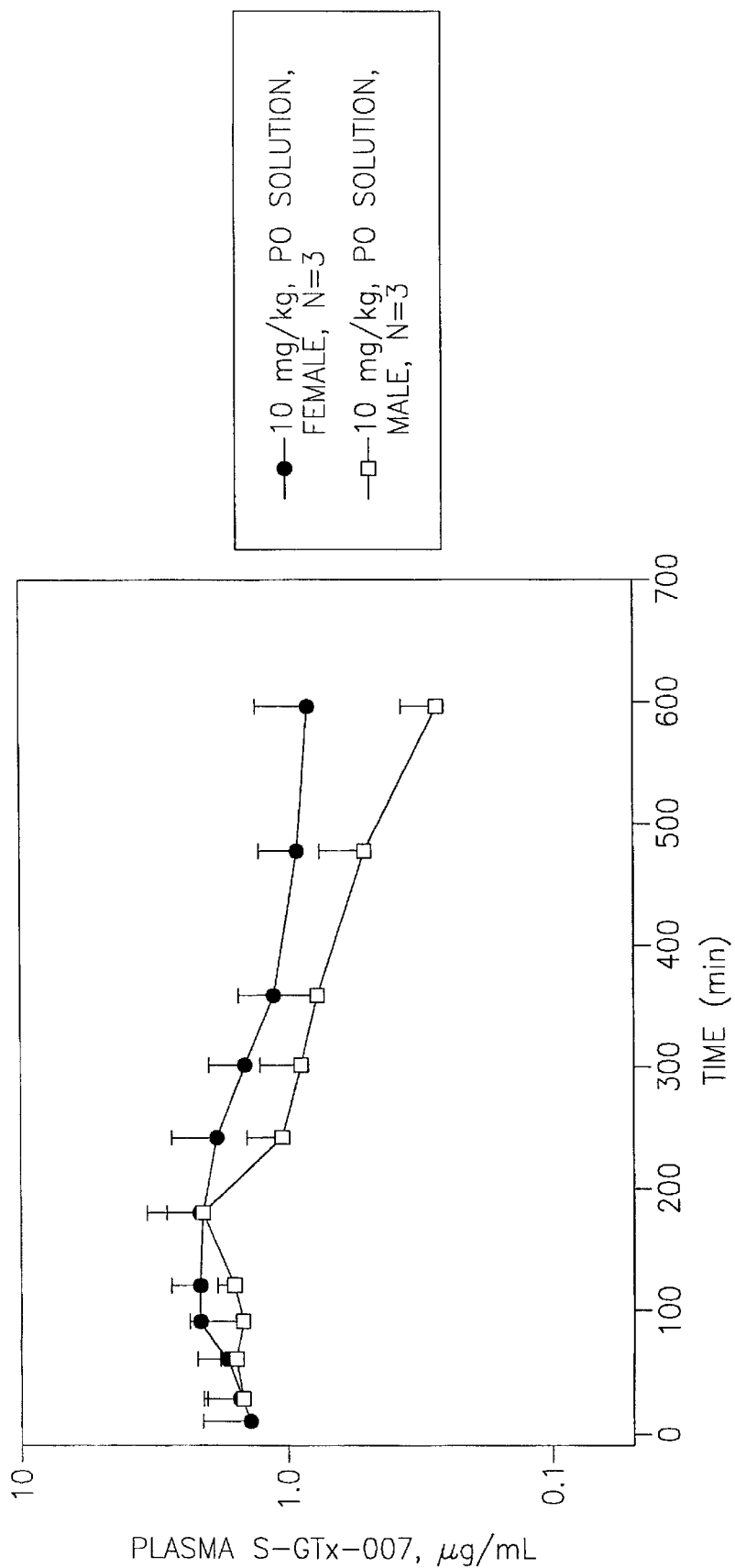
FIG. 5: Average plasma concentration-time profiles of S-GTx-007 in beagle dogs after PO administration as solution at 10 mg/kg.
Figure 6:
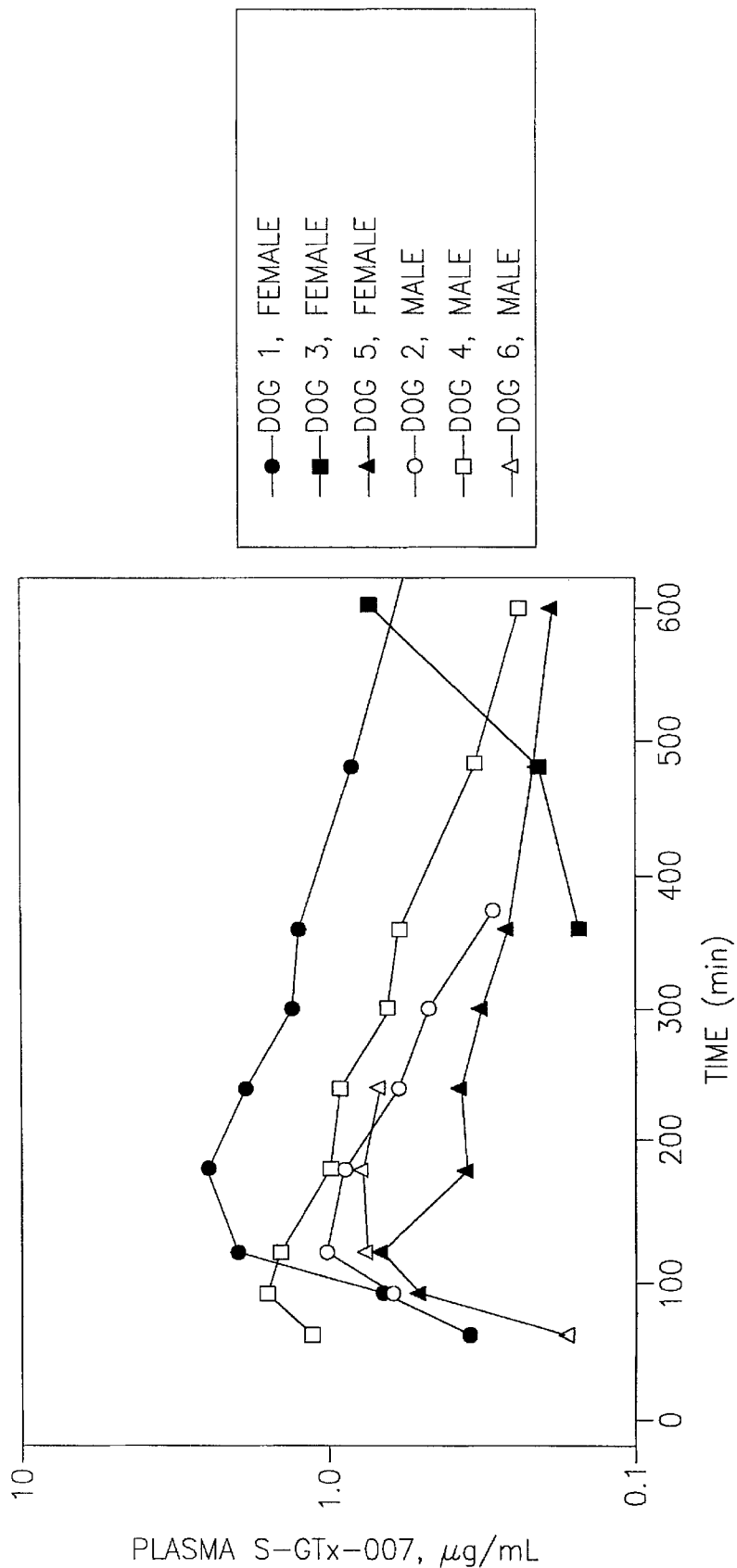
FIG. 6: Average plasma concentration-time profiles of S-GTx-007 in beagle dogs after IV administration as capsules at mg/kg.

The pharmacokinetics of S-GTx-007, a novel selective androgen receptor modulator or (SARM), were characterized in beagle dogs. A four-treatment, four-period crossover design was utilized in the study, which involved a total of six beagle dogs, three of each gender. Each animal received a 3 mg/kg IV dose, a 10 mg/kg IV dose, a 10 mg/kg PO dose in solution, and a 10 mg/kg PO dose in capsule, in a randomly assigned order. There was an one-week washout period between treatments. Plasma samples were collected for up to 72 hr after drug administration. Plasma S-GTx-007 concentrations were analyzed by a validated HPLC method. The clearance (CL), volume of distribution (Vss), half-life ($T_{1/2}$), and other pharmacokinetic parameters were determined by noncompartmental methods. Results showed that S-GTx-007 was cleared from dog plasma with a terminal $T_{1/2}$ of about 4 hr and a CL of 4.4 mL/min/kg after IV administration. FIGS. 4, 5, and 6 show the plasma concentration-time profiles of S-GTx-007 after administration of an intravenous solution, oral solution, and oral capsule, respectively. The pharmacokinetics were dose- and gender-independent. The oral bioavailability of S-GTx-007 varied with the dosage form, and averaged 38% and 19% for solution and capsule, respectively. Thus, S-GTx-007 demonstrated moderate half-life, slow clearance and moderate bioavailability in beagle dogs, identifying it as the first of a new class of orally bioavailable tissue-selective androgen receptor modulators.

EXAMPLE 4
GTx-007 Analysis by HPLC

A reversed phase high pressure liquid chromatograph (HPLC) assay was developed to quantitate GTx-007 concentrations in dog plasma. Dog blood samples were obtained by venipuncture and centrifuged at 1000 g for 15 minutes. Samples were stored frozen at −20° C. until analysis. Individual samples were rapidly thawed and an aliquot (0.5 ml) was spiked with internal standard (20 μl of a 200 μg/ml aqueous solution of CM-II-87). An aliquot of 1 ml of acetonitrile was added to the samples to precipitate plasma proteins. The samples were vortexed and then centrifuged at 1000 g for 15 minutes. The supernatant was decanted into glass extraction tubes and 7.5 ml of ethyl acetate was added. The extraction mixture was left at room temperature for 20 minutes, and vortexed several times during this interval. The samples were then centrifuged at 1000 g for 10 minutes, and the organic phase was removed and placed in conical-bottomed glass tubes. The organic phase was evaporated under nitrogen. The samples were reconstituted in 200 μl of mobile phase (35:65 acetonitrile:water) and transferred to an autosampler vial for HPLC injection (Waters 717 plus autosampler, Waters Corp., Milford, Ma.). The isocratic mobile phase of 35% (v/v) acetonitrile in water was pumped at a flow rate of 1 ml/min (Model 510, Waters Corp.). The stationary phase was a C18 reversed phase column (Novapak C18, 3.9×150 mm). Analytes were monitored with UV detection at 270 nm (Model 486 absorbance detector, Waters Corp.). Retention times for GTx-007 and CM-II-87 were 11.1 and 16.9 minutes, respectively. Chromatography data was collected and analyzed using Millennium software. Plasma concentrations of GTx-007 in each sample were determined by comparison to calibration curves. Calibration curves were constructed by adding known amounts of GTx-007 to dog plasma. Final GTx-007 concentrations in dog plasma samples used in the calibration curves were 0.08, 0.2, 0.4, 2, 4, 10, and 20 μg/ml. Calibration curves were linear over this concentration range and exhibited correlation coefficients (r2) of 0.9935 or greater. Intra- and inter-day coefficients of variation for the standards ranged from 6.4% for 0.08 μg/ml to 7.9% for 20 μg/ml.

Melting points were determined on a Thomas-Hoover capillary melting point apparatus and are uncorrected. Infrared spectra were recorded on a Perkin Elmer System 2000 FT-IR. Optical rotations were determined on an Autopols II® Automatic Polarimeter (Rudolph Research Model III-589-10, Fairfield, N.J.). Proton and carbon-13 magnetic resonance spectra were obtained on a Broker AX 300 spectrometer (300 and 75 MHz for $^1$H and $^{13}$C, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica get on aluminum plates (silica gel 60 F 254, 20×20 cm, Aldrich Chemical Company Inc., Milwaukee, Wis.). Flash chromatography was performed on silica gel (Merck, grade 60, 230–400 mesh, 60) Tetrahydrofuran (THF) was dried by distillation over sodium metal. Acetonitrile (MeCN) and methylene chloride ($CH_2Cl_2$) were dried by distillation from $P_2O_5$.

What is claimed is:

1. A selective androgen receptor modulator compound having in-vivo androgenic and anabolic activity of a non-steroidal ligand for the androgen receptor having the formula:

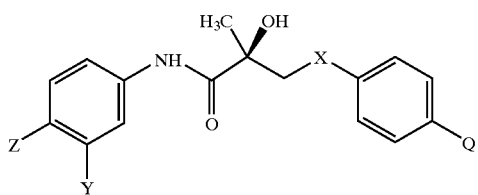

where
X is a O,
Z is $NO_2$, CN, COR, or CONHR;

Y is I, $CF_3$, Br, Cl, or $SnR_3$;
R is an alkyl group or OH; and
Q is acetamido or trifluroacetamido.

2. The selective androgen receptor modulator compound of claim 1, wherein Z is $NO_2$.

3. The selective androgen receptor modulator compound of claim 1, wherein Y is $CF_3$.

4. The selective androgen receptor modulator compound of claim 1, wherein Q is $NHCOCH_3$.

5. The selective androgen receptor modulator compound of claim 1, wherein X is $NO_2$, Y is $CF_3$, and Q is $NHCOCH_3$.

* * * * *

UNITED STATES PATENT AND TRADEMARK OFFICE
CERTIFICATE OF CORRECTION

PATENT NO. : 6,492,554 B2
DATED : December 10, 2002
INVENTOR(S) : Dalton, James T. et al.

Page 1 of 1

It is certified that error appears in the above-identified patent and that said Letters Patent is hereby corrected as shown below:

<u>Title page,</u>
Item [63] should read -- Continuation Application No. 09/644,970, filed on August 24, 2000, which was converted to Provisional Application Serial No. 60/367,355. --

<u>Column 1,</u>
Lines 5-9, should read -- This application is a Continuation Application of U.S. Serial No. 09/644,970, filed August 24, 2000, which was converted to Provisional Application Serial No. 60/367,355, and claims priority of U.S. Ser. No. 60/300,083, filed June, 25, 2001, which are hereby incorporated by reference. --
Line 10, should read -- This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention. --

Signed and Sealed this

Twenty-fourth Day of February, 2004

JON W. DUDAS
*Acting Director of the United States Patent and Trademark Office*